US009181564B2

(12) United States Patent
Leonetti et al.

(10) Patent No.: US 9,181,564 B2
(45) Date of Patent: Nov. 10, 2015

(54) USE OF BACTERIA FOR THE PRODUCTION OF BIOENERGY

(75) Inventors: Jean-Paul Leonetti, Castelnau-le-Lez (FR); Ivan Matic, Boulogne-Billancourt (FR); Jacques Biton, La Croix Saint-Ouen (FR); Philippe Pouletty, Paris (FR)

(73) Assignees: DEINOVE, Paris (FR); CENTRE NATIONAL DE LA RECHERCHE SCIENTIFIQUE (CNRS), Paris (FR); UNIVERSITE MONTPELLIER 1, Montpellier (FR)

( * ) Notice: Subject to any disclaimer, the term of this patent is extended or adjusted under 35 U.S.C. 154(b) by 537 days.

(21) Appl. No.: 12/740,404

(22) PCT Filed: Nov. 14, 2008

(86) PCT No.: PCT/EP2008/065613
§ 371 (c)(1),
(2), (4) Date: Jan. 19, 2011

(87) PCT Pub. No.: WO2009/063079
PCT Pub. Date: May 22, 2009

(65) Prior Publication Data
US 2011/0104766 A1  May 5, 2011

(30) Foreign Application Priority Data

Nov. 14, 2007  (FR) ..................... 07 08005

(51) Int. Cl.
*C12P 7/06* (2006.01)
*C12N 1/12* (2006.01)

(52) U.S. Cl.
CPC . *C12P 7/065* (2013.01); *Y02E 50/17* (2013.01)

(58) Field of Classification Search
None
See application file for complete search history.

(56) References Cited

U.S. PATENT DOCUMENTS

| 6,102,690 | A | 8/2000 | Ingram et al. |
| 2011/0104766 | A1 | 5/2011 | Leonetti et al. |
| 2011/0294979 | A1 | 12/2011 | Leonetti et al. |
| 2011/0306085 | A1 | 12/2011 | Isop et al. |
| 2012/0052540 | A1 | 3/2012 | Biton et al. |
| 2012/0058533 | A1 | 3/2012 | Biton et al. |

FOREIGN PATENT DOCUMENTS

| EP | 2218773 | 8/2010 |
| KR | 100836093 | 6/2008 |
| WO | WO 95/27064 | 10/1995 |
| WO | WO 97/10352 | 3/1997 |
| WO | WO 01/023526 | 4/2001 |
| WO | WO 02/059351 | 8/2002 |
| WO | WO 2006/131734 | 12/2006 |
| WO | WO 2007/128338 | 11/2007 |
| WO | WO 2009/063079 | 5/2009 |
| WO | WO 2010/081899 | 7/2010 |
| WO | WO 2010/094665 | 8/2010 |
| WO | WO 2010/130806 | 11/2010 |
| WO | WO 2010/130812 | 11/2010 |
| WO | WO2011/107506 | 9/2011 |

OTHER PUBLICATIONS

Christopher D. Skory, Isolation and expression of lactate dehydrogenase genes from *Rhizopus oryzae.*, Appl Environ Microbiol Jun. 2000;66(6):2343-8.*
Fontaine et al. Molecular characterization and transcriptional analysis of adhE2, the gene encoding the NADH-dependent aldehyde/alcohol dehydrogenase responsible for butanol production in alcohologenic cultures of *Clostridium acetobutylicum* ATCC 824.,J Bacteriol. Feb. 2002;184(3):821-30.*
Brim, H. et al. "Engineering *Deinococcus radiodurans* for metal remediation in radioactive mixed waste environments" *Nature Biotechnology*, Jan. 2000, pp. 85-90, vol. 18, XP-002491111.
Ferreira, A. C. et al. "*Deinococcus geothermalis* sp. Nov. and *Deinococcus murrayi* sp. nov., Two Extremely Radiation-Resistant and Slightly Thermophilic Species from Hot Springs" *International Journal of Systematic Bacteriology*, Oct. 1997, pp. 939-947, vol. 47, No. 4, XP-022491109.
Henstra, A. M. et al. "Microbiology of synthesis gas fermentation for biofuel production" *Current Opinion in Biotechnology*, 2007, pp. 200-206, vol. 18, XP-22110181.
John, R. P. et al. "Fermentative production of lactic acid from biomass: an overview on process developments and future perspectives" *Appl. Microbiol. Biotechnol.*, 2007, pp. 524-534, vol. 74, XP-002464997.
Klapatch, T. R. et al. "Organism Development and Characterization for Ethanol Production Using Thermophilic Bacteria" *Applied Biochemistry and Biotechnology*, 1994, pp. 209-223, vol. 45/46, XP-009104255.
Lynd, L. R. "Production of Ethanol from Lignocellulosic Materials Using Thermophilic Bacteria: Critical Evaluation of Potential and Review" *Advances in Biochemical Engineering*, 1989, pp. 1-52, vol. 38, XP-9104256.
Makarova, K. S. et al. "Genome of the Extremely Radiation-Resistant Bacterium *Deinococcus radiodurans* Viewed from the Perspective of Comparative Genomics" *Microbiology and Molecular Biology Reviews*, Mar. 2001, pp. 44-79, vol. 65, No. 1, XP-002491113.
Makarova, K. S. et al. "*Deinococcus geothermalis*: The Pool of Extreme Radiation Resistance Genes Shrinks" *PLOS ONE*, Sep. 2007, pp. 1-21, vol. 9, XP-002491112.
Meima, R. et al. "Promoter Cloning in the Radioresistant Bacterium *Deinococcus radiodurans*" *Journal of Bacteriology*, May 2001, pp. 3169-3174, vol. 183, No. 10, XP-002491110.

(Continued)

*Primary Examiner* — Iqbal H Chowdhury
(74) *Attorney, Agent, or Firm* — Saliwanchik, Lloyd & Eisenschenk

(57) ABSTRACT

The present invention relates to composition and methods of producing bioenergy. More specifically, the invention relates to the use of bacterium of the genus *Deinococcus* and/or related genera for the modification of biomass or biomass derivatives with a view to producing bioenergy products and metabolites.

21 Claims, 4 Drawing Sheets

(56) References Cited

OTHER PUBLICATIONS

Figure 1:
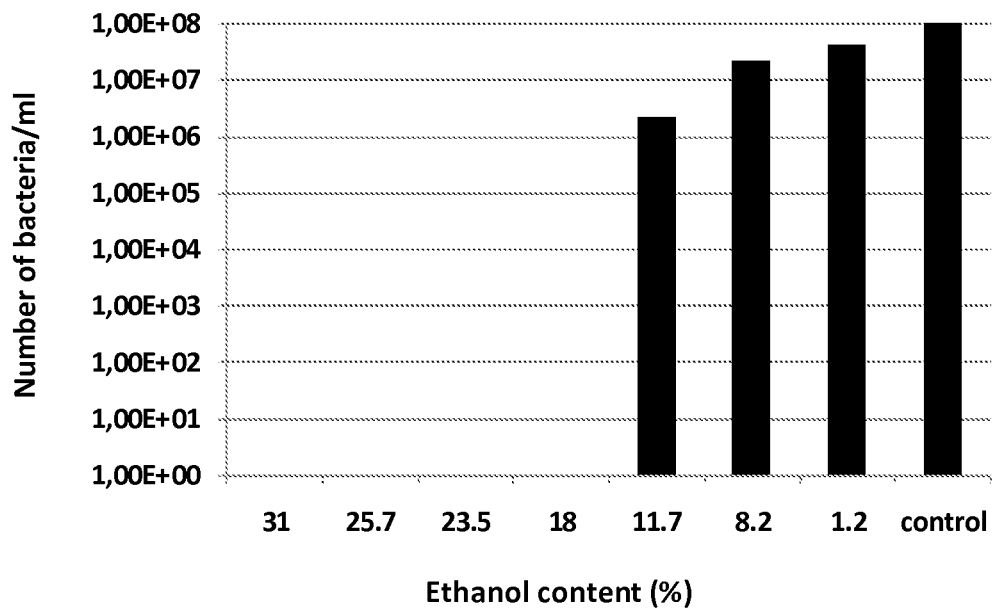

Smith, M. D. et al. "Gene expression in *Deinococcus radiodurans*" *Gene*, 1991, pp. 45-52, vol. 98, XP-002938523.
Zahradka, K. et al. "Reassembly of shattered chromosomes in *Deinococcus radiodurans*" *Nature*, Oct. 5, 2006, pp. 569-573, vol. 443, XP-002491114.
Harish, V. et al. "Xylanase Production by Ultra Violet Induced Variants of *Streptomyces fradiae* SCF-5" *Journal of Food Science and Technology*, Jan. 1, 1978, pp. 243-246, vol. 15, No. 6.
Alea, F. et al. "Selection of hypercellulolytic derepressed mutants of *Cellulomonas* sp." *Applied Microbiology and Biotechnology*, 1991, pp. 643-645, vol. 35, No. 5.
Temp, U. et al. "A Small-Scale Method for Screening of Lignin-Degrading Microorganisms" *Applied Environmental Microbiology*, Apr. 1998, pp. 1548-1549, vol. 64, No. 4.
Zenoff, V. F. et al. "Diverse UV-B Resistance of Culturable Bacterial Community from High-Altitude Wetland Water" *Current Microbiology*, May 1, 2006, pp. 359-362, vol. 52, No. 5.
Pavlikova, E. et al. "Improvement of the Basidiomycete *Coprinus* sp." *Folia Microbiologica*, Jan. 1, 1982, pp. 126-130, vol. 27, No. 2.
Written Opinion in International Application No. PCT/EP2010/051885, Aug. 23, 2010, pp. 1-10.
Omelchenko, M. et al. "Comparative genomics of *Thermus thermophilus* and *Deinococcus radiodurans*: divergent routes of adaptation to thermophily and radiation resistance" *BMC Evolutionary Biology*, 2005, pp. 1-22, vol. 5, No. 57.
Rainey, F. et al. "Extensive Diversity of Ionizing-Radiation-Resistant Bacteria Recovered from Sonoran Desert Soil and Description of Nine New Species of the Genus *Deinococcus* Obtained from a Single Soil Sample" *Applied and Environmental Microbiology*, Sep. 2005, pp. 5225-5235, vol. 71, No. 9.
Weisburg, W.G. et al. "The *Deinococcus-thermus* Phylum and the Effect of rRNA Composition on Phylogenetic Tree Construction" *Systematic and Applied Microbiology*, 1989, pp. 128-134, vol. 11.
Database EMBL, Accession No. M21413, "*D. radiodurans* 16s ribosomal RNA gene" XP002633260, Nov. 23, 1989, p. 1.
Suihko, M.L. et al. "Characterization of aerobic bacterial and fungal microbiota on surfaces of historic Scottish monuments" *Systematic and Applied Microbiology*, 2007, pp. 494-508, vol. 30.
Database EMBL, Accession No. EF093134, "*Deinococcus* sp. VTT E-052909 16S ribosomal RNA gene, complete sequence" XP002633261, Aug. 7, 2007, pp. 1-2.
Database EMBL, Accession No. AM283039, "*Deinococcus* sp. Han23 partial 16S rRNA gene, strain Han23" XP002633262, Jun. 26, 2006, p. 1.
Rainey, F. et al. "Phylogenetic Diversity of the Deinococci as Determined by 16S Ribosmal DNA Sequence Comparison" *International Journal of Systemic Bacteriology*, Apr. 1997, pp. 510-514, vol. 47, No. 2.
Written Opinion in International Application No. PCT/EP2011/053089, Mar. 2, 2010, pp. 1-7.
Berdy, J. "Bioactive Microbial Metabolites—A personal view" *Journal of Antibiotics*, Jan. 1, 2005, pp. 1-26, vol. 58, No. 1.
Singh, S. et al. "Biodiversity, chemical diversity and drug discovery" *Progress in Drug Research*, 2008, pp. 142-174, vol. 65.
Yang, B. et al. "Effects of microwave irradiation on isolation of soil actinomycetes" *Yingyong Shengtai Xuebao*, May 2008, pp. 1091-1098, vol. 19, No. 5.
Sinha, R. et al. "UV-protectants in cyanobacteria" *Plant Science*, Dec. 23, 2007, pp. 278-289, vol. 174, No. 3.
Chung, B. et al. "Effects of low-dose gamma-irradiation on production of shikonin derivatives in callus cultures of *Lithospermum erythrorhizon* S." *Radiation Physics and Chemistry*, Sep. 1, 2006, pp. 1018-1023, vol. 75, No. 9.

Ghosal, D. et al. "How radiation kills cells: Survival of *Deinococcus radiodurans* and *Shewanella oneidensis* under oxidative stress" *FEMS Microbiology Reviews*, Apr. 2005, pp. 361-375, vol. 29.
Dib, J. et al. "Occurrence of Resistance to Antibiotics, UV-B, and Arsenic in Bacteria Isolated from Extreme Environments in High-Altitude (Above 4400 m) Andean Wetlands" *Current Microbiology*, May 2008, pp. 510-517, vol. 56, No. 5.
Keller, M. et al. "Tapping Into Microbial Diversity" *Nature Reviews*, Feb. 2004, pp. 141-150, vol. 2, No. 2.
Reichenbach, H. "Myxobacteria, producers of novel bioactive substances" *Journal of Industrial Microbiology & Biotechnology*, Jan. 1, 2001, pp. 149-156, vol. 27. No. 3.
Bibb, M. "Regulation of secondary metabolism in streptomycetes" *Current Opinion in Microbiology*, 2005, pp. 208-215, vol. 8, No. 2.
Written Opinion in International Application No. PCT/EP2010/050513, Apr. 24, 2010, pp. 1-10.
Kolari, M. et al. "Colored moderately thermophilic bacteria in paper-machine biofilms" *Journal of Industrial Microbiology and Biotechnology*, Apr. 2003, pp. 225-238, vol. 30, No. 4.
Written Opinion in International Application No. PCT/EP2010/056600, May 14, 2009, pp. 1-8.
Weon, H. et al. "*Deinococcus cellulosilyticus* sp. nov., isolated from air" *International Journal of Systematic and Evolutionary Microbiology*, Aug. 1, 2007, pp. 1685-1688, vol. 57, No. Part 8.
Zhang, Y.-M. et al. "Induction of a Futile Embden-Meyerhof-Parnas Pathway in *Deinococcus radiodurans* by Mn: Possible Role of the Pentose Phosphate Pathway in Cell Survival" *Applied and Environmental Microbiology*, Jan. 2000, pp. 105-112, vol. 66, No. 1.
Holland, A. et al. "Development of a defined medium supporting rapid growth for *Deinococcus radiodurans* and analysis of metabolic capacities" *Applied Microbiology and Biotechnology*, Mar. 31, 2006, pp. 1074-1082, vol. 72, No. 5.
Anonymous. "Conference de presse: Présentation des projets de DEINOVE dans le domaine des biocarburants et des activités de DEINOLAB, laboratoire coopératif créé par DEINOVE, le CNRS et l'Université de Montpellier" Oct. 15, 2008, pp. 1-10, XP-002591932.
Written Opinion in International Application No. PCT/EP2010/056592, Jul. 29, 2010, pp. 1-7.
Written Opinion in International Application No. PCT/EP2008/065613, Jan. 28, 2009, pp. 1-8.
Office Action dated Jan. 7, 2013 in U.S. Appl. No. 13/145,246.
Office Action dated Jan. 2, 2013 in U.S. Appl. No. 13/320,048.
Cox, M. et al. "*Deinococcus radiodurans*—The Consummate Survivor" *Nature Reviews in Microbiology*, Nov. 2005, pp. 882-892, vol. 3.
Panesar, P. et al. "Comparison of ethanol and temperature tolerance of *Zymomonas mobilis* strain in glucose and molasses medium" *Indian Journal of Biotechnology*, Jan. 2007, pp. 74-77, vol. 6.
Office Action dated Dec. 4, 2012 in U.S. Appl. No. 13/319,526.
Chica, R. et al. "Semi-rational approaches to enginnering enzyme activity: combining the benefits of directed evolution and rational design" *Current Opinion in Biotechnology*, 2005, pp. 378-384, vol. 16.
Sen, S. et al. "Developments in Directed Evolution for Improving Enzyme Functions" *Appl Biochem Biotechnol*, 2007, pp. 212-223, vol. 143.
Sanchez, A. et al. "Efficient Succinic Acid Production from Glucose through Overexpression of Pyruvate Carboxylase in an *Escherichia coli* Alcohol Dehydrogenase and Lactate Dehydrogenase Mutant" *Biotechnol. Prog.*, 2005, pp. 358-365, vol. 21, No. 2.
Manaia, C. et al. "Characterization of halotolerant *Thermus* isolates from shallow marine hot springs on S. Miguel, Azores" *Journal of General Microbiology*, 1991, pp. 2643-2648, vol. 137.

* cited by examiner

USE OF BACTERIA FOR THE PRODUCTION OF BIOENERGY

CROSS-REFERENCE TO RELATED APPLICATION

This application is the U.S. national stage application of International Patent Application No. PCT/EP2008/065613, filed Nov. 14,2008, the disclosure of which is hereby incorporated by reference in its entirety, including all figures, tables and amino acid or nucleic acid sequences.

FIELD OF INVENTION

The present invention relates to composition and methods of producing bioenergy. More specifically, the invention relates to the use of bacteria of the genus *Deinococcus* and/or related genera for the modification of biomass or biomass derivatives with a view to producing bioenergy products and metabolites.

BACKGROUND OF INVENTION

It is known to use microorganisms to conduct modification of biomass, essentially plant biomass, to produce bioenergy products, for example ethanol.

Current industrial processes only allow the culture and growth of microorganisms for the fermentation and extraction of ethanol at temperatures in the region of 30° C., owing to the fragility of the industrial microorganisms (yeasts) used. They also entail major bioenergy costs to concentrate the ethanol after fermentation, since the yeasts currently used for this fermentation cannot withstand concentrations of more than 100 g/l. Additionally, the fermentation of these yeasts practically only uses C6 sugars, of glucose type.

It is also known to treat biological material, bacterial strains inter alia, to impart improved properties thereto.

For example, U.S. Pat. No. 6,716,631 of S. Del Cardayre et al. describes a method based on iterative cycles of recombination and selection/screening to confer desired properties to whole cells and to whole organisms. The added properties are, for example, increased aptitude for genetic recombination, enhanced genome copy number, increased capacity to express and/or secrete proteins and secondary metabolites.

By taking a molecular genetics approach, the authors propose techniques to modify suitably the genomes of cells and organisms to impart novel, improved properties thereto.

The method described in U.S. Pat. No. 6,716,631 uses a population of different cells, the culturing of these cells to form hybrid cells by protoplast fusion, then the screening or selecting of cells which evolved towards acquiring a desired property, and the repeating of these steps until at least one cell is obtained that has the desired modification. This method is presented as being an advantageous alternative to known methods based on a strain improvement programme.

The protoplasts subjected to said fusion may derive from prokaryotic organisms.

One of the envisaged applications in this US patent is the fermentation for the production, e.g. of ethanol, whose yield and cost it is proposed to improve using said recombination method by shuffling the DNA of the microorganisms used. By way of example, mention is made of the homologous recombination of *Rhodococcus*, known to catalyze two-phase reactions.

International patent application No. WO01/023526 describes the production and use of bacteria resistant to radiation and able to operate bioremediation, in particular of the genus *Deinococcus* (notably *D. radiodurans* and *D. geothermalis*), modified so as be more efficient for the metabolizing, degradation or detoxifying of inorganic and organic contaminants, such as radionuclides, heavy metals and organic solvents. It is recommended that these bacteria should be manipulated to express heterologous enzymes able to detoxify said elements. The bacterial strains are manipulated to combine a variety of functions encoded by different genes in a single host.

US patent application of I. Narumi et al., published on Sep. 18, 2003 under No. 2003/0175977, describes an endogenous plasmid derived from a strain of *D. radiopugnans*, pUE30, which can be used as vector able to replicate autonomously in bacteria of genus *Deinococcus*, and which can be used to construct a shuttle vector also containing a plasmid able to replicate autonomously in *E. coli* and its derivatives, and able to replicate in a bacterium both of genus *Deinococcus* and of *E. coli*.

U.S. Pat. No. 7,160,715 of C. B. Fliermans describes means to measure the distribution and frequency of in vivo generation of DNA strand breaks. These means comprise the use of a PprA protein derived from *Deinococcus radiodurans*.

US patent application published under No. 2004/0224320 on behalf of K. Satoh et al describes a Gram-positive bacterium (Access No ATCC BAA-149 or a mutant thereof) that is isolated and purified. The isolate is able to degrade a large variety of organic contaminants and is suitable for the bioremediation of a variety of organic contaminations, in the presence of ionizing radiation.

Also, a recent monograph on the production of ethanol using fermentation with strains of microorganisms was published under the title "Ethanol Fermentation Strains" by J. R. Hettenhaus, under the aegis of the United States Department of Energy and the National Renewable Energy Laboratory (Dec. 16, 1998). In this document, which summarizes the contributions made by participants in the study concerned, it is pointed out that:

the only micro-organism strains which can be used in existing equipment should be similar to those already used, namely *Saccharomyces, Zymomonas* and *E. coli*;

in the short term, the increased fermentation of xylose and arabinose could be the targeted objective, it being specified however that it is of little interest to increase the converting efficacy of the other sugars of hexose or oligomer type;

over the longer term, gains could be achieved regarding higher operating temperatures and combining of the steps of enzyme production, saccharification and hydrolysis.

There was therefore a need for a method to ferment biomass and to obtain ethanol and optionally other metabolites, which could be implemented under significantly better operating conditions than those of current methods, and which at the same time could be more easily piloted than known methods and capable of leading to fermentation products that are cheaper and easier to upgrade.

The invention is able to bring solutions to these expectations and to provide improved methods to draw benefit from biomass by producing alternative bioenergy products, which are becoming increasingly necessary due to the significant reduction in energy sources of fossil origin.

SUMMARY OF THE INVENTION

The present invention relates to methods and compositions for producing bioenergy products or metabolites. More specifically, the invention relates to the use of particular microorganisms for producing bioenergy products or metabolites from biomass or derivatives thereof. The invention derives inter alia from the discovery that microorganisms of the genus *Deinococcus* have unexpected and advantageous properties for modification or conversion of biomass or biomass derivatives with a view to obtaining compounds which can be used to produce bioenergy, ethanol in particular, on an industrial scale and both economically and reliably.

An object of the present invention therefore resides in a method of production of bioenergy products or metabolites comprising contacting a biomass or biomass derivatives with a native or modified bacterium having the capacity to reassemble its genome, in full or in part, when disrupted by a stress, preferably a native or modified bacterium of the genus *Deinococcus*, or an extract thereof.

A further object of this invention is a method of converting biomass or biomass derivatives into bioenergy products or metabolites comprising treating said biomass or biomass derivatives in the presence of a bacterium of the genus *Deinococcus* or a bacterium having the capacity to reassemble its genome, in full or in part, when disrupted by a stress, or an extract thereof.

In a particular aspect, the present invention relates to a method comprising the following steps:
a) culturing and/or growing said bacterium in aerobic and/or anaerobic conditions,
b) modifying a biomass or biomass derivatives into bioenergy products or metabolites of industrial interest (e.g., bioenergy sources such as ethanol, chemical building blocks such as succinic acid) using a composition comprising said bacterium or an extract thereof, and
c) collecting at least one bioenergy product or metabolite resulting from said modification of biomass or biomass derivatives.

This invention also relates to the use of a bacterium of the genus *Deinococcus* or an extract thereof for producing bioenergy products or metabolites from biomass or biomass derivatives.

The invention also relates to a composition comprising a *Deinococcus* bacterium and a biomass or biomass derivatives.

The invention also relates to bioenergy products produced using a method as described above.

The method of the invention can be performed using various native or modified *Deinococcus* species, such as, without limitation, *Deinococcus geothermalis*, *Deinococcus radiodurans*, *Deinococcus murrayi* or *Deinococcus cellulosilyticus*. The present invention shows that *Deinococcus* bacteria can efficiently promote the production of biofuels, such as ethanol, propanol, butanol glycerol, butanediol, propanediol, or organic acids of chemical interest and their salts, such as acetic acid, propionic acid, pyruvic acid, butyric acid, lactic acid and/or succinic acid or esters, in particular esters formed between the above-mentioned alcohols and acids.

The invention also unexpectedly shows that *Deinococcus* can be operated under conditions, such as elevated temperatures, a broad range of pH, presence of solvents, presence of raw substrates, suitable to produce high amounts of bioenergy products or metabolites from various substrates.

The invention thus provides novel methods and compositions for producing bioenergy products or metabolites in a very efficient manner.

LEGEND TO THE FIGURES

FIG. 1: Bactericide effect of ethanol on *Deinococcus geothermalis* DSM11301 in exponential growth phase: the bactericide potential of ethanol is significant for content higher than 8.2% in exponential growth phase.

Figure 2:
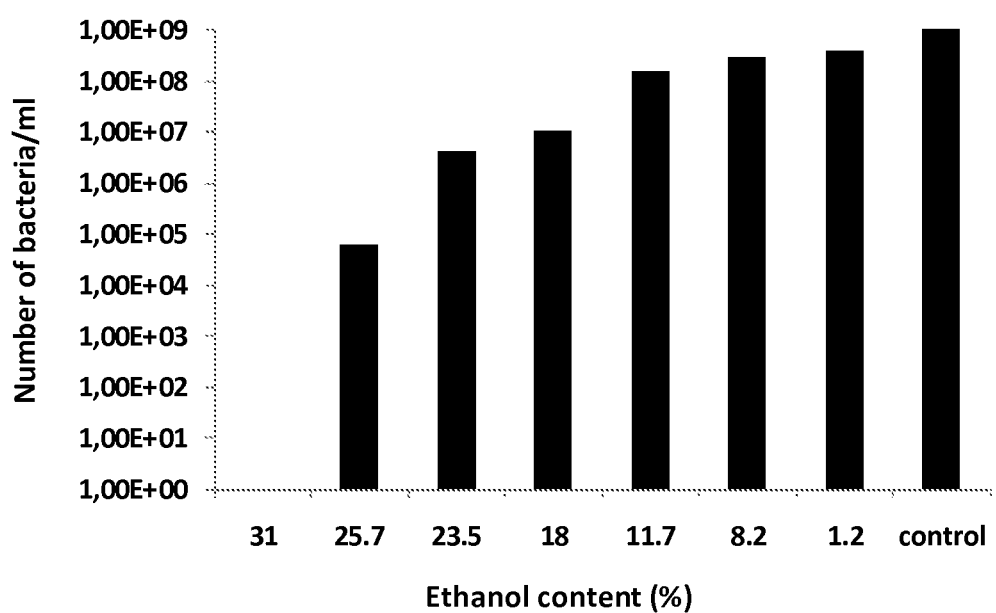

FIG. 2: Bactericide effect of ethanol on *Deinococcus geothermalis* DSM11301 in stationary phase: the bactericide potential of ethanol is significant for content higher than 11.7% in stationary phase.

Figure 3:
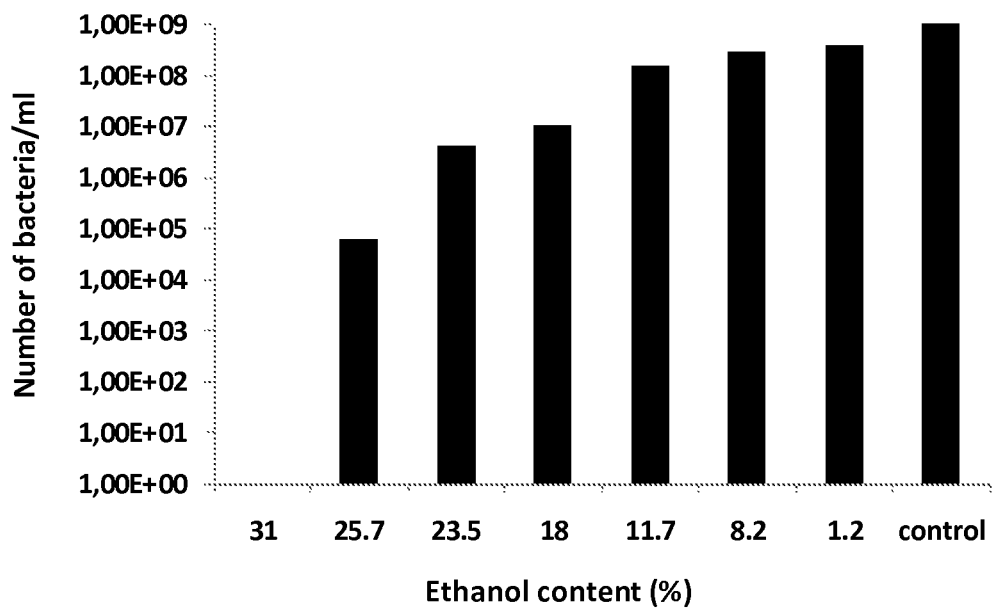

FIG. 3: Bactericide effect of butanol on *Deinococcus geothermalis* DSM11300 in exponential growth phase: the bactericide potential of butanol is significant for content higher than 1.5% in exponential phase.

Figure 4:
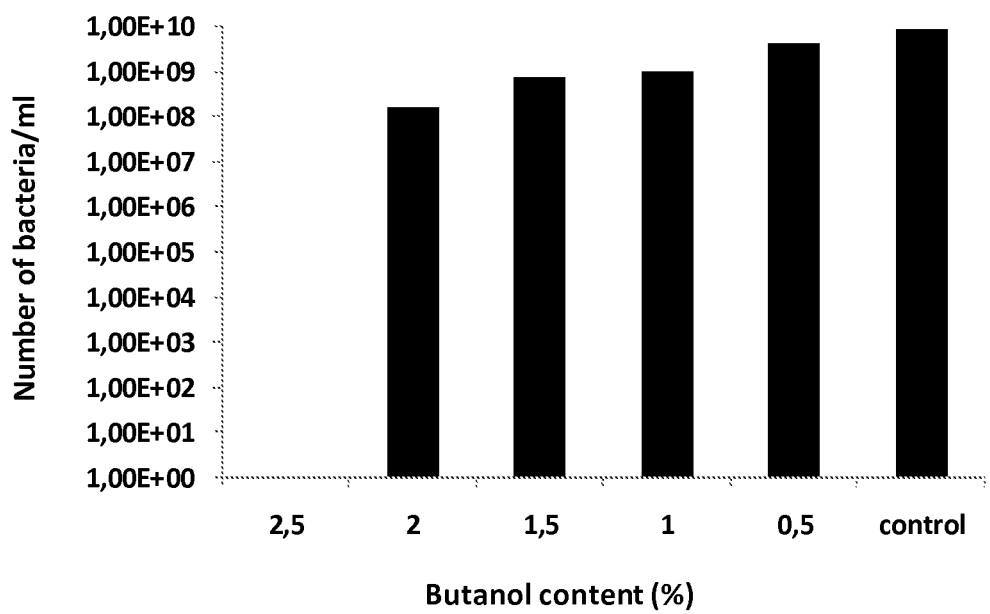

FIG. 4: Bactericide effect of butanol on *Deinococcus geothermalis* DSM11300 in stationary phase: the bactericide potential of butanol is significant for content higher than 2% in stationary phase.

Figure 5:
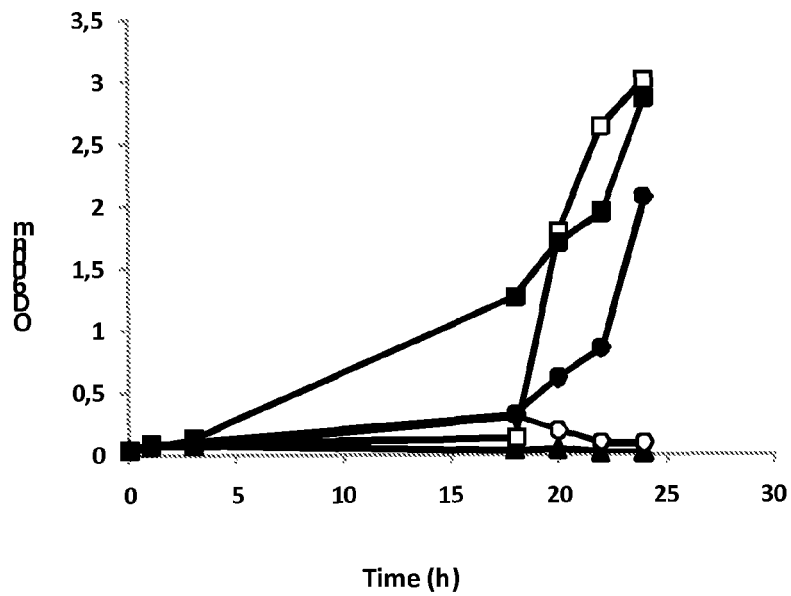

FIG. 5: Ethanol effect on *Deinococcus geothermalis* DSM11300 growth: black square, 0% ethanol; white square, 0.8% ethanol; black circle, 1.2% ethanol; white circle 2.4% ethanol; black triangle, 3.1% ethanol.

Figure 6:
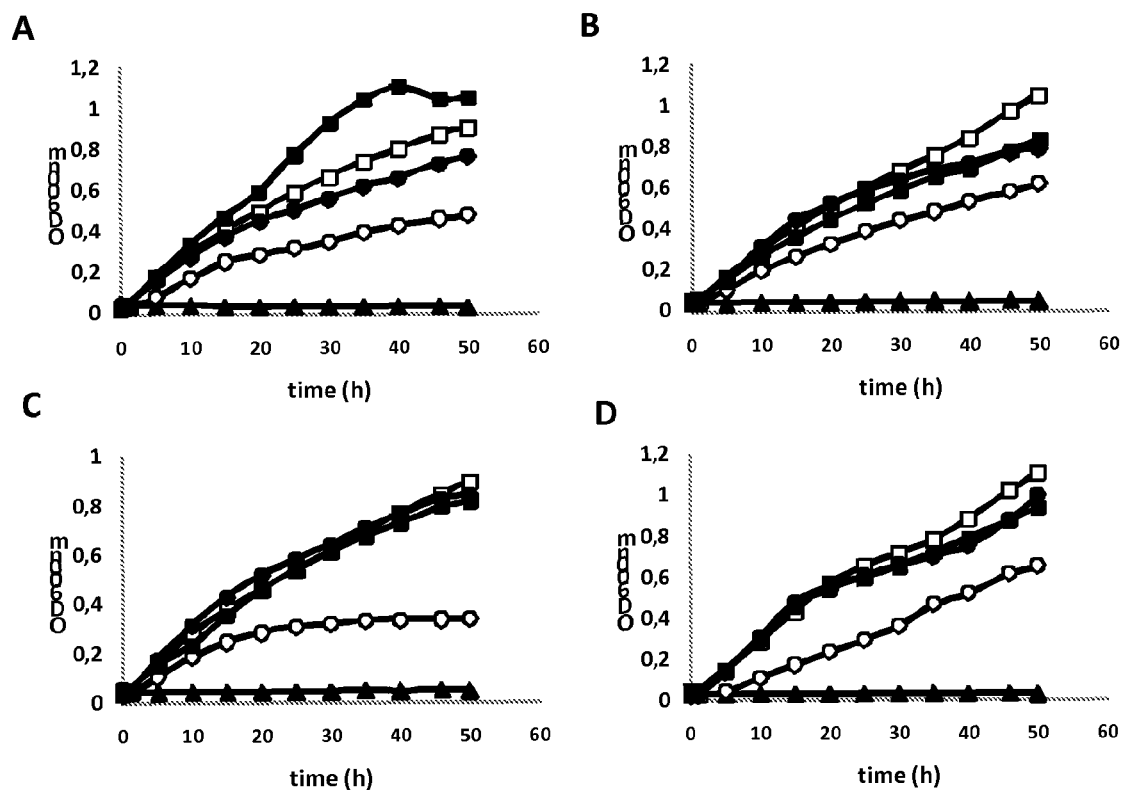

FIG. 6A: Effect of pH on the growth of *D. geothermalis* DSM 113000 (DRH05): black square, pH8; black circle, pH 7; white square, pH6; white circle, pH5; black diamond, pH4.

FIG. 6B: Effect of pH on the growth of *D. geothermalis* HAMBI 2481 (DRH37): black square, pH8; black circle, pH 7; white square, pH6; white circle, pH5; black diamond, pH4.

FIG. 6C: Effect of pH on the growth of *D. geothermalis* HAMBI 2480 (DRH38): black square, pH8; black circle, pH 7; white square, pH6; white circle, pH5; black diamond, pH4.

FIG. 6D: Effect of pH on the growth of *D. geothermalis* HAMBI 2411 (DRH39): black square, pH8; black circle, pH 7; white square, pH6; white circle, pH5; black diamond, pH4.

Figure 7:
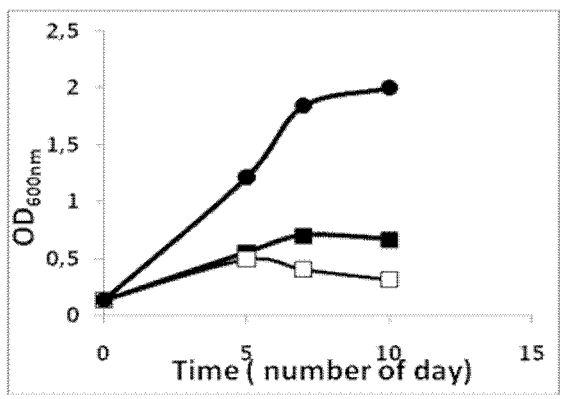

FIG. 7: Growth of *D. cellulosilyticus* in different liquid media. The bacteria were grown as described in material and methods of example 9. Black circle, growth in rich medium; black square, growth in CM-cellulose-containing minimal medium; white square, growth in minimal medium devoid of carbon source.

DETAILED DESCRIPTION OF THE INVENTION

The present invention relates to methods for the production of bioenergy products or metabolites using *Deinococcus* bacteria. The invention indeed shows that *Deinococcus* bacteria can produce bioenergy products or metabolites from biomass, in a very efficient way.

Definitions

In the context of the present application, the term "bacteria of the genus *Deinococcus*" includes wild type or natural variant strains of *Deinococcus* as well as recombinant strains, strains obtained through DNA-shuffling technologies or through directed evolution technologies.

An "extract of a bacterium" designates any fraction obtained from a bacterium, such as a cell supernatant, a cell debris, cell walls, DNA extract, enzymes or enzyme preparation or any preparation derived from bacteria by chemical, physical and/or enzymatic treatment, which is essentially free of living bacteria.

Within the context of the present invention, the term "bioenergy" designates a renewable energy derived from biomass. More specifically, the term "bioenergy products" designates "biofuels" and all final products of modification of biomass or biomass derivatives that can be used as fuels, such as ethanol. The term "metabolites" designates all possible intermediate molecules generated during the modification of biomass or biomass derivatives into bioenergy products, including but not limited to several chemical products of industrial interest, such as organic acids and building blocks.

Within the context of the present invention, the term "biomass" refers to living and recently dead biological material that can be used as fuel or for industrial production. Most commonly, biomass refers to plant matter grown to generate electricity or produce biofuels, but it also includes plant or animal matter used for production of fibers, chemicals or heat. Biomass may also include biodegradable wastes that can be burnt as fuel. The term biomass does not include organic material which has been transformed by geological processes into substances such as coal or petroleum.

Industrial biomass can be grown from numerous types of plants, including miscanthus, switchgrass, hemp, sugarbeet, wheat, corn, poplar, willow, sorghum, sugarcane, and a variety of tree species, ranging from eucalyptus to oil palm.

The biomass according to the invention comprises raw biomass and/or secondary biomass. The raw biomass is unprocessed material from biological matter. Examples include forestry products, such as mature trees unsuitable for lumber or paper production, agricultural products, such as grasses, crops and animal manure, and aquatic products, such as algae and seaweed. The secondary biomass is any material initially derived from raw biomass, which has undergone significant chemical and physical changes. Examples include paper, leather, cotton, hemp, natural rubber products, food processing by-products, and used cooking oils.

As used herein, the term "biomass derivatives" designates all molecules derived from raw biomass and/or from secondary biomass, as defined above, and in particular any material initially derived from raw biomass, which has undergone significant chemical and physical changes, such as for example, starch, cellulose, hemicelluloses and lignin.

As used herein, "intermediate platforms" are molecules obtained through physico-chemical or biochemical transformation of biomass derivatives, such as sugars, starch and bio-based synthetic gas (syngas).

Detailed Description

The present invention proposes to use *Deinococcus* bacteria to produce bioenergy products or metabolites from biomass. The present invention indeed shows that bacteria of the genus *Deinococcus* exhibit unexpected properties which allow them to cooperate in the production of bioenergy products or metabolites, by fermenting biomass or biomass derivatives.

*Deinococcus* bacteria have been shown to have the capacity to reassemble their genome, in full or in part, when disrupted by a stress (PCT/EP2006/005826 Radman-Zahradka). As mentioned before, these bacteria, particularly *D. radiodurans*, have been proposed for bioremediation. However, it has never been disclosed or suggested that *Deinococcus* bacteria would be able to produce bioenergy products and metabolites from biomass. In addition, it had never been suggested that *Deinococcus* bacteria having the required biological properties could be isolated and cultivated.

The invention now shows, for the first time, that it is possible to isolate or cultivate *Deinococcus* bacteria having at least one of the following properties, and that said bacteria are able to produce bioenergy products or metabolites:
 it is viable or functional at high temperatures (e.g., around 40-70° C.);
 it is viable or functional within a pH range from around 3 to around 9.5, preferably between around 4 and around 8;
 it is viable or functional in the presence of toxic agents, in particular organic solvents, e.g., ethanol;
 it is able to convert C6 and C5 sugars;
 it is able to promote cellulose digestion to yield glucose;
 it is able to promote hemicellulose digestion to yield xylose;
 it is able to grow in aerobic and/or anaerobic conditions in the presence of an appropriate carbon source.

Furthermore, *Deinococcus* bacteria are typically devoid of any pathogenicity and can therefore be used without specific confinement.

The invention thus discloses, for the first time, the ability of *Deinococcus* bacteria to make bioenergy products or metabolites from biomass, as well as their unexpected capacity to be grown and cultivated under specific conditions adapted to such use. The invention also proposes to use, for production of bioenergy products or metabolites, any bacteria having the capacity to reassemble their genome, in full or in part, when disrupted by a stress.

In a preferred embodiment, the method of this invention uses a thermophilic *Deinococcus* species, preferably selected from *Deinococcus geothermalis*, *Deinococcus radiodurans* and *Deinococcus murrayi*.

In a preferred embodiment of the invention, the method uses a *Deinococcus* bacterium viable in the presence of toxic agents, in particular in the presence of organic solvents, for example ethanol. The present application indeed shows that *Deinococcus* strains can be grown in the presence of high levels of solvents, such as ethanol or butanol, allowing production of biofuels in a more efficient way.

In another preferred embodiment of the invention, the method uses a bacterium that can be grown in a temperature range from approximately 40 to 70° C., preferably from 50° C. to 60° C. In a more preferred embodiment, the method uses a bacterium which can both be grown under elevated temperature (above 40° C.) and in the presence of a toxic agent or organic solvent, as disclosed above.

In a further particular embodiment of the present invention, the method uses a *Deinococcus* bacterium which can be viable or functional under concentration conditions of NaCl or equivalent salts possibly reaching around 5% weight/volume.

In another preferred embodiment of the invention, the method uses a bacterium which is viable in a pH interval between approximately 3 and 9.5, preferably between 4 and 8. Indeed, the inventors have discovered that *Deinococcus* strains can be maintained under such stringent conditions, which are particularly advantageous for converting biomass.

In a preferred embodiment, the invention uses a *Deinococcus* bacterium that is able to convert C6 and/or C5 sugars and/or to promote the digestion of cellulose to generate glucose and/or to promote the digestion of hemicellulose to generate xylose.

In a particular embodiment, invention relates to a method, wherein said *Deinococcus* bacterium is able to grow in the presence of xylan and to promote the digestion of xylan.

Such enzymatic activities, combined with a high thermoresistance, a broad range of pH tolerance and toxic agents tolerance, have never been reported before and are remarkable. As shown in the examples, *Deinococcus* bacteria having the above properties can be isolated, cultivated, and produce substantial amounts of bioenergy products or metabolites from biomass.

In this regard, another advantage of the invention resides in a method, wherein said *Deinococcus* bacteria are grown in a minimal medium containing C6 sugars, preferably glucose, or more complex sugars, preferably sucrose, cellobiose or starch, or C5 sugars, preferably xylose, as carbon source. A further advantage of the present invention resides in the fact that said *Deinococcus* bacteria can be grown in the presence of C3 carbohydrates, preferably, glycerol or sodium pyruvate.

Specific examples of bacteria suitable for use in the present invention are *Deinococcus geothermalis* strains with deposition no. DSM11300, DSM11301, DSM11302, HAMBI2480, HAMBI2481 and HAMBI2411; *Deinococcus murrayi* strains with deposition no. DSM11303 and DSM11305; or *Deinococcus cellulosilyticus* strain with deposition no. DSM18568$^T$ (listed in the Table 1), or strains substantially similar thereto or mutants thereof.

TABLE 1

List of *Deinococcus* strains

| Designation | Genus | Species | Ref | Code | Temp ° C. | Bibliographic Reference |
|---|---|---|---|---|---|---|
| DRH 05 | Deinococcus | geothermalis | DSM | 11300 | 45-50 | Ferreira et al, 1997 *Int J Syst Bacteriol*, 47(4): 939-47 |
| DRH 06 | Deinococcus | geothermalis | DSM | 11301 | 45-50 | Ferreira et al, 1997 *Int J Syst Bacteriol*, 47(4): 939-47 |
| DRH 07 | Deinococcus | geothermalis | DSM | 11302 | 45-50 | Ferreira et al, 1997 *Int J Syst Bacteriol*, 47(4): 939-47 |
| DRH 37 | Deinococcus | geothermalis | HAMBI | 2481 | 45-50 | Kolari et al, 2003 *J Ind Microbiol Biotechnol*, 30: 225-238 |
| DRH 38 | Deinococcus | geothermalis | HAMBI | 2480 | 45-50 | Kolari et al, 2003 *J Ind Microbiol Biotechnol* 30: 225-238 |
| DRH 39 | Deinococcus | geothermalis | HAMBI | 2411 | 45-50 | Väisänen et al, 1997, *Applied Microbiology* 84: 1069-1084 |
| DRH 08 | Deinococcus | murrayi | DSM | 11303 | 45-50 | Ferreira et al, 1997 *Int J Syst Bacteriol*, 47(4): 939-47 |
| DRH 10 | Deinococcus | murrayi | DSM | 11305 | 45-50 | Ferreira et al, 1997 *Int J Syst Bacteriol*, 47(4): 939-47 |
| DRH 46 | Deinococcus | cellulosilyticus | DSM | 18568$^T$ | 45 | Weon et al, 2007, *Int J of Syst & Evolutionary Microbiol*, 57, 1685-1688 |

All the strains listed in the table above are able to grow in a PGY-type culture medium at pH7. Other suitable culture media are disclosed in the experimental section.

It should be understood that additional *Deinococcus* strains having the properties as presently demonstrated and discovered can now be screened and identified by the skilled artisan, based on the teachings of the present application, e.g., by following guidance and tests as described in the experimental section.

As mentioned above, *Deinococcus* strains as used in the present application can be used either in native form, or modified (e.g., chemically or genetically) to acquire improved properties. In this regard, in a particular embodiment, the method uses a *Deinococcus* bacterium that is modified by accelerated evolution or by DNA shuffling technologies or by insertion of eukaryote, prokaryote or synthetic non-*Deinococcus* DNA or by insertion of another *Deinococcus* strain DNA, said modification affecting viability, growth or functions of the said bacterium in order to promote the modification of biomass.

In another embodiment of the invention, the bacterium used can be a recombinant or modified bacterial strain, advantageously using a method such as described in the international patent application No. PCT/EP2006/005826.

As discussed above, the invention shows that bacteria of the genus *Deinococcus*, or derivatives thereof, selected e.g., among *D. geothermalis*, *D. radiodurans* or *D. murrayi*, exhibit advantageous properties and are able to produce bioenergy products or metabolites from various raw substrates. The present invention therefore relates to the use of bacteria of the genus *Deinococcus* for the production of bioenergy products or metabolites from biomass or biomass derivatives. The present invention also relates to a method of producing bioenergy products or metabolites from biomass or biomass derivatives by exposing or culturing said biomass in the presence of bacteria of the genus *Deinococcus*, or an extract thereof, and recovering the bioenergy product or metabolite produced.

Culture or exposition can be made in any suitable condition or environment allowing modification of the biomass or derivative to produce bioenergy product. In this regard, the method can be performed in a reactor, in a fermentor, outdoor, in the presence of suitable nutrients or additives, if needed.

The method is typically conducted under pH conditions, temperature above 40° C., and in the presence of suitable substrates.

A particular object of this invention resides in a method comprising the following steps:
a) culturing and/or growing said bacterium in aerobic and/or anaerobic conditions,
b) modifying (e.g., converting or treating) biomass or biomass derivatives into bioenergy products or metabolites using a composition comprising said bacterium or an extract thereof, and
c) collecting at least one bioenergy product or metabolite resulting from said modification of biomass or biomass derivatives.

Another object of the invention resides in a method to convert biomass or biomass derivatives using at least one bacterium or bacterial extract such as defined above or a composition such as described above, comprising a combination of:
at least one operation of placing in culture and developing said bacterial strain or said bacterial strain extract under suitable growth and development conditions,
at least one operation to convert biomass or a biomass derivative under the action of suitable quantities of said bacterial strain or said bacterial strain extract, under conditions suitable for said conversion of biomass, or biomass derivates, and
collecting at least one bioenergy product or metabolite derived from said conversion of biomass or biomass derivative, in particular collecting the ethanol thus produced.

In the above methods, the first step of culturing and/or growing said bacterium and the second step of modifying biomass or biomass derivatives into bioenergy products or metabolites using a composition comprising said bacterium or an extract thereof, can be carried out either simultaneously, or sequentially; the third step of collecting bioenergy products or metabolites can be carried out simultaneously with the first and/or the second step, or sequentially. In this regard, the biomass can be contacted with the bacterium under suitable conditions to allow expansion of said bacterium, thereby increasing the efficiency of the process. Alternatively, bacterial strains can be expanded separately, under suitable culture conditions, and subsequently added to the biomass. It should be understood that the precise amounts of bacteria used initially in order to efficiently transform biomass into substantial bioenergy products or metabolites can be adjusted by the skilled artisan depending on the type of bacteria, the type of biomass or derivatives, and the culture conditions.

In a particular embodiment of the method according to the invention, the *Deinococcus* bacteria are grown separately from biomass conversion.

In another particular embodiment, the method uses a composition comprising a *Deinococcus* bacterium or an extract thereof and at least one suitable additive or excipient, preferably at least one agent chosen from the group consisting of anti-foam agents and nutrient agents. Suitable anti-foam agents are dispersants, detergents and surfactants in particular, and more generally amphiphilic compounds.

In a particular embodiment, the method of the invention is performed in a reactor of conversion of biomass. By "reactor" is meant a conventional fermentation tank or any apparatus or system for biomass conversion specially designed to implement the invention and therefore consisting in particular of bioreactors, biofilters, rotary biological contactors, and other gaseous and/or liquid phase bioreactors for the treatment of biomass or biomass derivatives. The apparatus which can be used according to the invention can be used continuously or in batch loads.

In the reactor, to implement the method of the invention, at least one bacterium or bacterial extract of the invention is used, and/or at least one composition such as defined above, whilst said reactor is arranged and supplied so that physicochemical conditions are set up and maintained therein so that said bacterium is operational for the application under consideration and so that, optionally, bacterial growth is possible and preferably promoted therein.

In another embodiment of the method of the invention, the bacteria are grown in a reactor, during the conversion of biomass or biomass derivatives, whilst suitable physicochemical conditions are set up and maintained for this bacterial growth to be possible, and preferably promoted. For example, a 500 ml Erlenmeyer can be used in the presence of 100 ml of 167 Thermus medium or minimum medium described below at a temperature of 50° C.

In alternative embodiments of the invention, the conversion of biomass or biomass derivatives is conducted under aerobiosis, anaerobiosis or under micro aerobiosis.

According to a further aspect, the object of the invention is a reactor for the conversion of biomass or biomass derivatives, using at least one *Deinococcus* bacterium or bacterial extract such as defined above, or a composition such as defined above.

The process of this invention can be used to produce bioenergy from various types of biomass. In a preferred embodiment, the biomass comprises wood and wood residues, forest residues, paper mill residues, agricultural crops, agricultural residues, edible and/or non-edible plants or parts thereof, straw, garden wastes, aquatic plants, animal wastes, livestock operation residues, manure, organic municipal wastes and/or industrial organic wastes. Biomass may also include biodegradable wastes.

In a particular embodiment, the invention concerns a method of modifying biomass or biomass derivatives or intermediate platforms into bioenergy products or metabolites, wherein the biomass derivatives are preferably lignin, cellulose, hemicellulose, starch, and wherein intermediate platforms are preferably carbohydrates, such as xylan, glucuronoxylan, arabinoxylan, glucomannan, xyloglucan, starch, sucrose, lactose, maltose, trehalose, glucose, xylose, mannose, arabinose, rhamnose, galactose and/or fructose.

A particular object of the invention resides in a method for the production of biofuels. Within the context of the present invention, the term "biofuel" designates a fuel derived from a leaving or recently dead biological carbon source. The biofuel may be produced from renewable resources, especially plant or animal biomass, or from municipal and industrial wastes. The biofuel according to the invention comprises "first generation biofuel" and/or "second generation biofuel".

The first generation biofuels are obtained from vegetable or animal organic material, preferably from sugar, starch, vegetable oil or animal fats. The main source for the production of first generation biofuels are edible plants or parts thereof. The first generation biofuels include vegetable oil, biodiesel, bioalcohols, biogas, syngas and solid biofuels. Bioalcohols include ethanol, propanol and butanol. More preferably, the method of the invention is used for the production of ethanol, propanol, butanol. The most preferred biofuel is ethanol.

The second generation biofuels are produced preferably from non-edible plants or non-edible parts of plants. They include non food crops, biomass wastes, stalks of wheat, corn and wood. Preferably, the biofuel according to the invention include cellulosic bio fuels.

Depending on the starting biomass, the production of bioenergy products or metabolites, such as biofuel, can require two successive steps: a step of hydrolysis, catalyzed by enzymes, preferably cellulases or laccases, which break down long, complex-carbohydrate chains, such as cellulose or lignin respectively, into smaller fermentable sugars; and a step of fermentation, which further breaks down organic compounds, such as sugars, into alcohols. It should be pointed out that *Deinococcus* strains according to the present invention may be used for either one or both of said reactions. Indeed, the invention shows that *Deinococcus* can hydrolyze long carbohydrate chains (e.g., xylan or cellulose) and can also produce metabolites (e.g., ethanol, glycerol, butanediol, propanediol, as well as acetic, propionic, pyruvic and butyric acids) from C3, C5 or C6 sugars. If desired, however, it should be noted that *Deinococcus* strains may be used in combination with any other bacterial strains.

The following examples are given for purposes of illustration and not by way of limitation.

EXAMPLES

Example 1

Selection Tests

To determine whether a microorganism is equipped with the properties required by the invention, specific tests must be conducted in order to determine whether a genus, a species and/or a bacterial strain is able to have the required properties and to function in a method for the conversion of biomass or biomass derivatives, and to determine which significant improvements can thereby be obtained.

These specific tests according to the invention are conducted in the following conditions:

Culture Medium:

*D. geothermalis* (D.G.) is cultured at 50° C. under agitation, in an aerobic medium. The 167 culture medium is used to maintain the strains. The minimum medium is used in fermentation experiments, in particular to characterize the metabolites. In this case, 500 ml of culture medium are incubated 1 to 7 days under agitation in a 1 L Erlenmeyer, after being seeded with 5 ml of D. G. confluent culture.

167 Thermus Medium

| | |
|---|---|
| Tryptone | 1 g |
| Yeast extract | 1 g |
| Agar | 28 g |
| Nitrilotriacetic acid | 100 mg |
| $CaSO_4 \times 2\ H_2O$ | 40 mg |
| $MgCl_2 \times 6\ H_2O$ | 200 mg |
| 0.01 M Fe citrate | 0.5 ml |
| Solution of trace elements (see below) | 0.5 ml |
| Phosphate buffer (see below) | 100 ml |
| $H_2O$ | 900 ml |
| Adjust to pH 7.2 with NaOH, autoclave at 121° C. for 15 min. | |
| autoclave the phosphate buffer separately and add to the medium | |

Phosphate Buffer

| | |
|---|---|
| $KH_2PO_4$ | 5.44 g |
| $Na_2HPO_4 \times 12\ H_2O$ | 43 g |
| $H_2O$ | 1000 ml |
| Adjust to pH 7.2 | |

Solution of Trace Elements

| | |
|---|---|
| $H_2SO_4$ | 0.5 ml |
| $MnSO_4 \times H_2O$ | 2.28 g |
| $ZnSO_4 \times 7\ H_2O$ | 0.5 g |
| $H_3BO_3$ | 0.5 g |
| $CuSO_4 \times 5\ H_2O$ | 25 mg |
| $Na_2MoO_4 \times 2\ H_2O$ | 25 mg |
| $CoCl_2 \times 6\ H_2O$ | 45.00 mg |
| $H_2O$ | 1000 ml |

Minimum Medium

MOPS Buffer

| | |
|---|---|
| MOPS acid | 400 mM |
| $NH_4Cl$ | 200 mM |
| NaOH | 100 mM |
| KOH | 100 mM |
| $CaCl_2$ | 5 M |
| $K_2SO_4$ | 276 mM |
| $MgCl_2$ | 5.28 mM |
| pH 7, filtered, sterilised | |

Carbon Source

| | |
|---|---|
| Glucose | 160 mM |
| Filtered, sterilised | |

Phosphate

| | |
|---|---|
| $K_2HPO_4$ | 12.3 mM |
| $KH_2PO_4$ | 7.7 mM |
| Filtered, sterilised | |

Vitamins

| | |
|---|---|
| D-biotin | 10 μM |
| Niacine | 10 μM |
| Pyridoxal-HCl | 10 μM |
| Thiamine-HCl | 10 μM |
| Store at pH 4, filtered, sterilised | |

Solution of Trace Elements

| | |
|---|---|
| $H_2SO_4$ | 5 ml |
| $MnSO_4 \times H_2O$ | 22.8 g |
| $ZnSO_4 \times 7\ H_2O$ | 5 g |
| $H_3BO_3$ | 5 g |
| $CuSO_4 \times 5\ H_2O$ | 250 mg |
| $Na_2MoO_4 \times 2\ H_2O$ | 250 mg |
| $CoCl_2 \times 6\ H_2O$ | 450 mg |
| $H_2O$ | 1000 ml |
| Filtered, sterilised | |

Iron Source

| | |
|---|---|
| $FeCl_3$ | 200 M |
| Sodium citrate | 200 M |
| Filtered, sterilised | |

Amino Acids

| | |
|---|---|
| Ser | 100 mM |
| Gln | 100 mM |
| Filtered, sterilised | |

These storage solutions in the concentrated 10× state are diluted extemporaneously.

Detection of the Laccase Activity of the Bacterium

Principle:

$$\text{Syringaldazine} + O_2 \xrightarrow{\text{Laccase}} \text{Oxidized Syringaldaxine} + 2H_2O$$

Reagents:
A. 100 mM Potassium Phosphate buffer, pH 6.5 at 30° C.
B. 0.216 mM Syringaldazine (3 ml are prepared in absolute ethanol from Syringaldazine obtained from Sigma Prod., No. S-7896.)
C. Enzyme

| | test | blank |
|---|---|---|
| $H_2O$ | 0.50 ml | Non-fermented medium, 0.5 ml or dilution |

-continued

|           | test                                    | blank    |
|-----------|-----------------------------------------|----------|
| Reagent A | 2.20 ml                                 | 2.20 ml  |
| Reagent B | 0.3 ml                                  | 0.3 ml   |
| Reagent C | Fermented medium, 0.5 ml or dilution    | 0        |

The increase in optical density is recorded at 530 nm.

Under these conditions, one unit of enzyme produces an increase in optical density of 0.001 per minute at pH 6.5 and at 30° C.

Detection of the Cellulase Activity of the Bacterium:

Principle:

The test is based on follow-up of the conversion of NAD into NADH during degradation of the cellulose. An increase in absorbency is then monitored at 340 nm following the supplier's instructions, available on the internet link: (See Worldwide Website: sigmaaldrich.com/img/assets/18160/Cellulase.pdf)

Detection of Ethanol Production:

Ethanol is quantified using two methods.

Enzymatic Method:

$$\text{Ethanol} + \text{NAD} \xrightarrow{\text{ADH}} \text{Acetaldehyde} + \text{NADH}$$

This method is based on follow-up of the conversion of NAD into NADH in the presence of ethanol and alcohol dehydrogenase.

This reaction translates as in increase in absorbency at 340 nm. For this measurement, the Sigma N7160, kit was used following the manufacturer's instructions available on the Internet link:

sigmaaldrich.com/sigma/bulletin/N7160BUL.pdf).

Measurement by Reverse Phase High Performance Liquid Chromatography

Conditions:

HPLC Gilson with automatic injector, detection by refractometry,

Column: Phenomenex Rezex ROA, 300 mm×7.8 mm

Column temperature: 65° C.

Mobile phase: 0.005 N sulphuric acid

Flow rate: 0.600 ml/min

First a calibration curve is made by injecting culture medium containing known concentrations of ethanol into the column. The peak area eluted at 22.26 min corresponding to ethanol is measured. A calibration curve is plotted.

Next, the quantity of ethanol produced by the bacterium is measured by injecting the culture supernatant into the column. The peak area eluted at 22.26 min and corresponding to ethanol is measured. The concentration of ethanol present in the supernatant is deduced by comparison with the calibration curve.

The detection and quantification of the other metabolites possibly produced in diverse proportions can be made following conventional methods of analysis and evaluation.

Bacteria are haploid organisms which reproduce by binary division and which feed on mineral and organic substances found in the environment.

Their gas requirements, especially with respect to oxygen, are varied and the culture and fermentation techniques to be used must be adapted according to whether they are strict aerobic, strict anaerobic or facultative aero-anaerobic microorganisms.

The activity of cellulase, advantageously required by the invention, takes part in the degradation of cellulose, whilst the activity of laccase allows or facilitates the degradation of lignin.

The production, from fermentation of biomass, of bioenergy products such as ethanol in particular and/or other metabolites is performed following the operating conditions being adapted subsequent to iterative tests to the conditions and parameters of the technique of the present invention, which are in particular, the quantities of bacterial culture medium, the operating conditions of temperature and/or pressure, and the options of aerobic, anaerobic or microaerobic fermentation. Following the specific tests and assays described above, the selected natural or genetically modified strains are implemented according to the method of the invention.

Example 2

Production of Ethanol in the Presence of *Deinococcus geothermalis*

In a 500 ml Erlenmeyer, containing 100 ml minimum medium at 50° C., an inoculum of $10^{10}$ *D. geothermalis* (DG) is added at 50° C. The culture is placed under agitation to promote aeration.

This culture is then ready to be used in a conventional biomass fermentation tank in which, under the best conditions, ethanol and other metabolites can be obtained with an excellent yield at 55° C.

After 1 to 7 days in the reactor with the biomass to be treated, the presence of the above-mentioned ethanol and metabolites was quantified by HPLC (following the protocol described above). Disappearance of glucose was observed and concomitant production of ethanol, whose concentration was estimated analytically. Other metabolites of interest were detected. The replacement of glucose by xylose in the culture medium also allows bacterial growth and the production of ethanol.

In one variant of embodiment of this example, similar results can be obtained by conducting both bacterial culture and fermentation in the same tank.

Example 3

Bactericide Effects of Ethanol and Butanol on *Deinococcus geothermalis*

Material and Methods

This method enables evaluation of the bactericide effects of organic solvents on bacteria in growth or in stationary phase. The solvents tested are ethanol and butanol. The bacteria tested belonging to the genus *Deinococcus*:

develop between 40 and 70° C.

are operational between pH3 and pH9.5 are able to reassemble, in full or in part, their genome split by a stress, notably by irradiation, in particular by UV or gamma rays, by dessiccation, by enzyme action, by ultrasound or by chemical stress.

The test is to be carried out at the optimal growth temperature for the strain tested. From a pre-culture in stationary phase in an enriched medium, 10 ml of enriched medium is seeded at 1% v/v. The enriched medium contains: peptone 2 g/l, yeast extract 5 g/l and glucose 10 g/l: solution sterilized by autoclaving (20 minutes at 120° C.). To this solution are added the following solutions: MOPS buffer (10×) pH7 [acid MOPS 400 mM, NH$_4$Cl 200 mM, NaOH 1000 mM, KOH 100 mM, CaCl$_2$ 5 µLLM, Na$_2$SO$_4$ 2.76 mM, MgCl$_2$ 5.28 mM]; micronutriments (10000×) [(NH$_4$)$_6$(Mo$_7$) 24 300 mM, H$_3$BO$_3$ 4 mM, CoCl$_2$ 0.3 mM, CuSO$_4$ 0.1 mM, MnCl$_2$ 2.5 mM, ZnSO$_4$ 0.1 mM]; FeCl$_3$(100×) 20 mM in C$_6$H$_5$Na$_3$O$_7$ 20 mM; K$_2$HPO$_4$ 1 g/l: solutions sterilized by filtration (45 µm).

200 µl of culture are distributed on a 96-well microplate. To avoid any phenomenon of solvent evaporation, the microplate is covered with an impervious sterile film.

Once the exponential growth phase (optical density of 0.5 at 600 nm), or once the stationary phase (plateau), is reached, the solvent is added. The content tested is 0 to 31% for ethanol and 0 to 2.5% for butanol. The culture is then incubated under agitation for one hour.

Count: At the end of incubation, and for each concentration in solvent, 20 µl of culture are transferred onto another microplate and are diluted in cascade (dilutions at 1/10 over 9 wells). The dilution culture medium is an enriched medium. 5 µl of each dilution are laid in triplicate on PGY agar medium. peptone 5 g/l, yeast extract 2.5 g/l, glucose 0.5 g/l, agar 14 g/l: medium sterilized by autoclaving 20 minutes at 120° C. Once growth permits, for each percentage of solvent tested, a count is carried out to evaluate the influence of organic solvents on the strain.

Results

The concentration of solvent at which we consider there is a loss of bacterial viability corresponds to the minimum concentration of solvent at which we observe the loss of one log in relation to the control.

The strains tested (FIGS. 1 to 4) present satisfactory resistance to the solvents from the perspective of an industrial application in a fermenter.

Example 4

Growth of Bacteria in the Presence of C3, C5 and C6 Carbon Sources

Material and Methods

Pre-cultures were carried out either in medium A containing peptone (2 g/l), yeast extract (5 g/l), glucose (10 g/l) or in PGY medium. After centrifugation of the culture medium, the bacterial pellet was washed twice with minimal medium A to eliminate all sources of nutriment in the inoculum. This inoculum was used to seed (1/66) culture medium A (200 µl) containing one of the following sources of carbon at 1% (w/v): D(+)glucose, D(+)cellobiose, sucrose, starch, D(+)xylose, xylan from birch wood, glycerol, sodium pyruvate. In the case of strains DRH07, DRH39, DRH08 and DRH10, glutamate (10 mM) was added to the culture medium. Bacterial growth was conducted at 45° C. on 96-well microplates under agitation and followed by measuring the optical density at 544 nm using a spectrophotometer (Chameleon multilabel detection Platform plate, ScienceTec) or at 600 nm using a spectrostar OMEGA microplate reader (BMG Labtech).

References of carbon sources used: Xylan from birch wood (95588, Fluka), cellobiose (22150, Fluka), D(+)xylose (95730, Fluka), glucose (G8270-1KG, Sigma), sucrose (S9378-1KG, Sigma), starch (S9765-500G, Sigma), glycerol (453752, CarloErba), sodium pyruvate (Sigma).

Composition and Preparation of Culture Media

PGY Medium: Peptone (10 g/l), glucose (1 g/l), yeast extract (5 g/l), the mixture is autoclaved for 20 minutes at 120° C.

Medium A: The various solutions used to prepare medium A were prepared from a stock solution sterilized by filtration:

A solution (pH7) containing: acid MOPS buffer 40 mM, NH$_4$Cl 20 mM, KOH 10 mM, NaOH 10 mM, CaCl$_2$ 0.5 µM, Na$_2$SO$_4$ 0.276 mM, MgCl$_2$ 0.528 mM.

A solution of micronutriments (pH5): (NH$_4$)$_6$(MO$_7$)$_{24}$ 3 nM, H$_3$BO$_3$ 400 nM, CoCl$_2$ 30 nM, CuSO$_4$ 10 nM, MnCl$_2$ 250 nM, ZnSO$_4$ 10 nM.

Solution of vitamins, pH4, (1 µg/l each): D-biotin, niacin, pyridoxal-HCl, thiamin-HCl, vitamin B12.

Source of phosphate: K$_2$HPO$_4$ 5.7 mM.

FeCl$_3$ 20 µM (prepared in a solution of sodium citrate then filtered).

Results

The bacteria listed in Table 2 (below) are able to multiply in a minimal culture medium (medium A) containing as the only source of carbon, sugar in C6 such as glucose, saccharose, cellobiose and starch. It should be noted that strains DRH37 and DRH06 are also able to grow in the presence of glycerol and sodium pyruvate (carbohydrates in C3).

The bacteria listed in Table 3 are also able to multiply in a minimal culture medium containing sugars in C5 (xylose or xylan) as the only source of carbon; with the exception of strains DRH06 and DRH07 which are not able to grow in the presence of xylan and xylose respectively.

TABLE 2

Test of assimilation of various sources of carbon in C6 and C3 carried out on various species of *D. geothermalis* and *D. murrayi*: − ΔOD < 0.2; + ΔOD = 0.2; ++ 0.3 ≥ ΔOD > 0.4; +++ 0.4 ≥ ΔOD ≥ 0.5; ++++ ΔOD ≥ 0.6.

| | *D. geothermalis* | | | | | | *D. murrayi* | |
|---|---|---|---|---|---|---|---|---|
| Carbon sources at 1% (w/v) | DRH05 | DRH06 | DRH07 | DRH37 | DRH38 | DRH39 | DRH08 | DRH10 |
| Carbohydrates in C6: | | | | | | | | |
| D-(+)-glucose | +++ | + | ++ | ++ | +++ | +++ | + | + |
| D-(+)-cellobiose | ++ | − | +++ | +++ | ++ | +++ | ++ | − |
| Sucrose | +++ | ++ | ++ | ++ | +++ | +++ | ++ | − |
| Starch | +++ | ++ | ++ | ++ | +++ | − | ++ | − |
| Carbohydrates in C3: | | | | | | | | |
| Glycerol | − | − | − | ++ | − | − | − | − |
| Sodium Pyruvate | − | + | − | − | − | − | − | − |

ΔOD corresponds to the difference between the value of OD at 544 nm at initial time T0 of growth and to the time T196 hours (approximately 8 days).

TABLE 3

Test of assimilation of various sources of carbon in C5 and C6 carried out on various species of *D. geothermalis* – ΔOD < 0.2; + ΔOD = 0.2; ++ 0.3 ≥ Δ OD > 0.4; +++ 0.4 ≥ Δ OD ≥ 0.5; ++++ Δ OD ≥ 0.6.

| Carbon source 1% (w/v) | DRH05 | DRH06 | DRH07 | DRH37 | DRH38 | DRH39 |
|---|---|---|---|---|---|---|
| D-(+)-glucose | +++ | ++ | + | ++++ | +++ | +++ |
| Xylan | +++ | – | + | ++++ | ++++ | ++++ |
| Xylose | +++ | +++ | – | ++++ | +++ | + |

Δ OD corresponds to the difference between the value of the OD at 600 nm at the initial time T0 of growth and at time T64 hours (approximately 2.5 days).

Example 5

Growth of bacteria in high ethanol concentration

Material and Methods

This method enables evaluation of the ability of a microorganism to develop in the presence of a high concentration of ethanol. The bacteria tested belonging to the species *Deinococcus geothermalis*:
   develop between 40 and 70° C.,
   are operational between pH3 and pH9.5,
   are able to reassemble, in part or in full, their genome split by a stress, notably by irradiation, in particular by UV or gamma rays, by dessication, by enzyme action, by ultrasound or by chemical stress.

The test is to be carried out at optimal growth temperature for the strain tested. From a pre-culture in stationary phase in an enriched culture medium, for each ethanol content to be tested, 20 ml of enriched medium is seeded at 1% v/v. The enriched culture medium contains: peptone 2 g/l, yeast extract 5 g/l and glucose 10 g/l: solution sterilized by autoclaving (20 minutes at 120° C.). To this solution are added the following solutions: MOPS buffer solution (10×) pH7 [acid MOPS buffer 400 mM, $NH_4Cl$ 200 mM, NaOH 1000 mM, KOH 100 mM, $CaCl_2$ 5 μM, $Na_2SO_4$ 2.76 mM, $MgCl_2$ 5.28 mM]; micronutriments (10000×) [$(NH_4)_6(Mo_7)$ 24 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; $FeCl_3$(100×) 20 mM in $C_6H_5Na_3O_7$ 20 mM; $K_2HPO_4$ 1 g/l: solutions sterilized by filtration (45 μm).

Ethanol is added at T0, the content varies from 0 to 31%. A follow-up of growth is carried out for each ethanol content tested. OD is read at 600 nm using a spectrophotometer (UV Light XS5, SECOMAM). An aliquot part of 1 ml of culture is taken at times: T0, T0+1H, T0+3H, T0+18H, T0+20H, T0+22H, T0+24H.

When it is necessary for reading, the culture is diluted to one tenth in enriched medium. Growth curves can be drawn for each ethanol content tested. At the end of the incubation period and for each ethanol content tested, a count is taken to assess the influence of the ethanol on the strain.

Results

Some strains tested, such as *Deinococcus geothermalis* DSM11300, are able to grow in a culture medium containing ethanol (see FIG. 5). Some strains, such as *Deinococcus geothermalis* DSM11300, show a resistance in culture media with a high ethanol content (see FIG. 6A).

Example 6

Production of Metabolites of Interest by *Deinococcus murrayi*

Material and Methods

This method enables evaluation of the ability of a microorganism to produce metabolites of interest (in the group consisting of glycerol, butanediol, propanediol, and acetic, propionic, pyruvic and butyric acids) from biomass or a derivative of biomass.

The bacteria tested belonging to the species *Deinococcus geothermalis*:
   develop between 40 and 70° C.,
   are operational between pH3 and pH9.5,
   are able to reassemble, in part or in full, their genome split by a stress, notably by irradiation, in particular by UV or gamma rays, by dessication, by enzyme action, by ultrasound or by chemical stress.

The test is to be carried out at optimal growth temperature for the strain tested. From a pre-culture (in stationary phase) prepared in an enriched culture medium, 20 ml of enriched medium are seeded: seeding at 1% v/v.

The enriched culture medium contains: peptone 2 g/l, yeast extract 5 g/l and glucose 10 g/l: solution sterilized by autoclaving (20 minutes at 120° C.). To this solution are added the following solutions: MOPS buffer solution (10×) pH7 [acid MOPS 400 mM, $NH_4Cl$ 200 mM, NaOH 1000 mM, KOH 100 mM, $CaCl_2$ 5 μM, $Na_2SO_4$ 2.76 mM, $MgCl_2$ 5.28 mM]; micronutriments (10000×) [$(NH_4)_6(Mo_7)$24 300 mM, $H_3BO_3$ 4 mM, $CoCl_2$ 0.3 mM, $CuSO_4$ 0.1 mM, $MnCl_2$ 2.5 mM, $ZnSO_4$ 0.1 mM]; $FeCl_3$(100×) 20 mM in $C_6H_5Na_3O_7$ 20 mM; $K_2HPO_4$ 1 g/l: solutions sterilized by filtration (45 μm).

The culture is left in an incubator, at 45° C., under agitation, until it reaches its stationary phase. Once the stationary phase is reached, the culture is centrifuged for 10 minutes at 4000 rpm. The supernatant is poured into another tube and is placed at −80° C. An HPLC UV analysis and refractometry (ion exchange column (H+)Biorad, mobile phase $H_2SO_4$ 5 mM, flow in mobile phase 0.6 ml/min, isocratic mode) enable the metabolites of interest to be identified.

Results

Some strains tested produce certain of the metabolites of interest sought (Table 4).

TABLE 4

Metabolites produced by *Deinococcus murrayi* DSM11305 (expressed in g/l).

| | GLUCOSE | ACETIC ACID | PROPIONIC ACID | PYRUVIC ACID |
|---|---|---|---|---|
| DRH10 CM | 7.76 | 0.138 | 1.044 | 0.043 |

Example 7

Growth of *Deinococcus geothermalis* in Various pH Conditions

Material and Methods

The strains are cultivated at 45° C. in PGY medium at different pH's. The pH was adjusted with $NH_3$ 10% (v/v) or HCl 10 N. Growth is followed by measuring optical density at 600 nm using a spectrostar microplate reader OMEGA, BMG Labtech.
Result Four strains (*D. geothermalis*) were able to multiply in a pH range between 5 and 8 (see FIGS. 6A, 6B, 6C and 6D).

Example 8

Isolation of UV-Resistant Thermophilic Bacteria from a Natural Environment

Treatment of Hot Water Samples

The hot water samples are concentrated by filtration over a 0.22 μm nitrocellulose filter (Millipore, France) then placed in suspension in 10 ml of sterile water. The filtered solution is then sonicated for approximately 60 seconds to resuspend the bacteria.

Treatment of Wood and Pebble Samples

The wood and pebble samples are immersed in sterile water then vortexed and sonicated for approximately 60 seconds.

Treatment of Samples of Stones, Moss, Lichen, Mud, Sediment, Biofilm, Soil and Animal Dejection The samples of moss, lichen, mud, soil and animal dejection are placed in suspension in sterile water (V/V) then vortexed. The samples are then sonicated for approximately 60 seconds.

Isolation of UV-Resistant Thermophilic Bacteria

Following sonication, between 500 μl and 2 ml, the suspensions are spread on a solid PGY-agar enriched culture medium sterilized by autoclaving (20 minutes at 120° C.) containing glucose (Sigma-Aldrich, France) 1 g/l, peptone (Fluka, France) 10 g/l and yeast extract (Fluka, France) 5 g/l. The seeded culture media then undergo 3 UV treatments using a BLX-E254 biolink (Vilber-Lourmat, France) of 4 mJ/cm$^2$ each carried out at an interval of 4 hours. After incubation at 45° C. for 3 to 4 days, the thermophilic colonies of interest are visible.

Example 9

Digestion of cellulose by *Deinococcus cellulosilyticus*

Material and Methods

A pre-culture of the strain *D. cellulosilyticus* was carried out in an enriched medium (see composition below). This pre-culture is used to seed (1% v/v) 10 ml of enriched medium, of minimal medium containing carboxymethyl cellulose (CM-cellulose), or this same medium devoid of carbon source.

Growth of bacteria was carried out at 30° C. in 50 ml Falcon tubes under agitation (110 rpm) and followed by measuring optical density at 600 nm with a spectrophotometer (WPA Biowave, Cell density Meter).

Enriched medium: peptone 2 g/l; yeast extract 5 g/l; glucose 10 g/l; a solution (pH7) containing: acid MOPS 40 mM, NH$_4$Cl 20 mM, KOH 10 mM, NaOH 10 mM, CaCl$_2$ 0.5 μM, Na$_2$SO$_4$ 0.276 mM, MgCl$_2$ 0.528 mM; a solution of micronutriments (pH5): (NH$_4$)$_6$(MO$_7$)$_{24}$ 3 nM, H$_3$BO$_3$ 400 nM, CoCl$_2$ 30 nM, CuSO$_4$ 10 nM, MnCl$_2$ 250 nM, ZnSO$_4$ 10 nM; a solution of vitamins, pH4, (1 μg/l each): D-biotin, niacin, pyridoxal-HCl, thiamin-HCl, vitamin B12; a source of phosphate: K$_2$HPO$_4$ 5.7 mM; FeCl$_3$ 20 μM.

Minimal medium: a solution (pH7) containing: MOPS acid 40 mM, NH$_4$Cl 20 mM, KOH 10 mM, NaOH 10 mM, CaCl$_2$ 0.5 μM, Na$_2$SO$_4$ 0.276 mM, MgCl$_2$ 0.528 mM; a solution of micronutriments (pH5): (NH$_4$)$_6$(MO$_7$)$_{24}$ 3 nM, H$_3$BO$_3$ 400 nM, CoCl$_2$ 30 nM, CuSO$_4$ 10 nM, MnCl$_2$ 250 nM, ZnSO$_4$ 10 nM; a solution of vitamins, pH4, (1 μg/l each): D-biotin, niacin, pyridoxal-HCl, thiamin-HCl, vitamin B12; a source of phosphate: K$_2$HPO$_4$ 5.7 mM; FeCl$_3$ 20 μM.

Result

It was demonstrated that the strain *D. cellulosilyticus* referenced with DSMZ under number DSM 18568$^T$ (Weon et al, 2007) possesses a CM-cellulose activity (Weon et al., 2007, international journal of Systematic and Evolutionary Microbiology, 57, 1685-1688.)

As is shown in FIG. 7, *D. cellulosilyticus* is able to multiply in a medium containing CM-cellulose as the only source of carbon; the variation in optical density at 600 nm after 10 days growth in this medium was significant ($\Delta DO_{600\,nm}$=0.5) compared with the control culture (medium devoid of carbon source; ($\Delta DO_{600\,nm}$=0.18). This result indicated that *D. cellulosilyticus* is not only able to degrade (depolymerise) CM-cellulose but also able to assimilate products derived from this degradation (cellobiose and glucose).

The invention claimed is:

1. A method of production of a biofuel comprising contacting vegetal biomass comprising xylan, cellulose and/or hemicellulose with a bacterium of the genus *Deinococcus* or with an extract of said bacterium, culturing said *Deinococcus* in contact with said vegetal biomass comprising xylan, cellulose and/or hemicellulose to produce a biofuel or reacting said extract with said vegetal biomass under conditions that permit the formation of a biofuel and collecting said biofuel, said biofuel being produced by said bacterium or extract thereof.

2. The method according to claim 1, said method comprising:
    a) culturing and/or growing said bacterium in contact with vegetal biomass under aerobic and/or anaerobic conditions; and
    b) collecting at least one biofuel.

3. The method according to claim 2, wherein steps a) and b) are carried out simultaneously or sequentially.

4. The method according to claim 2, wherein the biofuel is selected from ethanol, propanol, butanol, glycerol, butanediol, propanediol, or mixtures thereof.

5. The method according to claim 1, wherein the vegetal biomass is wood, wood residue, forest residue, mill residue, agricultural crop, agricultural residue, an edible and/or non-edible plant or parts thereof, straw, garden waste, an aquatic plant, or manure.

6. The method according to claim 1, wherein the vegetal biomass further comprises lignin, glucuronoxylan, arabinoxylan, glucomannan, xyloglucan, starch, sucrose, lactose, maltose trehalose, glucose, xylose, mannose, arabinose, rhamno, galactose and/or fructose.

7. The method according to claim 1, wherein said bacterium is viable in the presence of toxic agents or organic solvents.

8. The method according to claim 1, wherein said bacterium is grown in a temperature range from approximately 40 to 70° C.

9. The method according to claim 1, wherein said bacterium is viable or used in a pH interval between approximately 3 and 9.5.

10. The method according to claim 1, wherein said *Deinococcus* bacterium is able to convert C6 and/or C5 sugars and/or to promote the digestion of cellulose to generate glucose and/or to promote the digestion of hemicellulose to generate xylose.

11. The method according to claim 1, wherein said bacterium is *Deinococcus* geothermalis.

12. The method according to claim 11, wherein said Bacterium is *Deinococcus geothermalis* deposited as DSM11300.

13. The method according to claim 2, wherein said composition further comprises one or more antifoaming agents and/or nutrient agents.

14. The method according to claim 1, wherein a reactor for the conversion of vegetal biomass is employed.

15. The method according to claim 1, wherein the biofuel is selected from a vegetal oil, a biodiesel, a bioalcohol, a biogas, a syngas, a solid biofuel and a cellulosic biofuel.

16. The method according to claim 1, wherein the biofuel is a bioalcohol.

17. The method according to claim 1, wherein the vegetal Biomass comprises celluloses, hemicellulose or xylan.

18. The method according to claim 1, wherein the biofuel is ethanol.

19. The method according to claim 1, said method comprising:
  a) culturing and/or growing said bacterium with a liquid culture medium containing vegetal biomass under aerobic and/or anaerobic conditions; and
  b) separating at least one biofuel from the liquid culture medium.

20. The method according to claim 19, wherein the biofuel is a bioalcohol.

21. The method according to claim 19, wherein said bioalcohol is ethanol.

* * * * *

UNITED STATES PATENT AND TRADEMARK OFFICE
CERTIFICATE OF CORRECTION

Page 1 of 2

PATENT NO. : 9,181,564 B2
APPLICATION NO. : 12/740404
DATED : November 10, 2015
INVENTOR(S) : Jean-Paul Leonetti et al.

It is certified that error appears in the above-identified patent and that said Letters Patent is hereby corrected as shown below:

IN THE SPECIFICATION

Column 1,
Line 9, "14,2008" should read --14, 2008--.

Column 9,
Line 56, "under micro aerobiosis" should read --under microaerobiosis--.

Column 10,
Line 34, "cellulosic bio fuels" should read --cellulosic biofuels--.

Column 12,
Line 46, "10× state" should read --10X state--.
Line 52, "Oxidized Syringaldaxine" should read --Oxidized Syringaldazine--.

Column 14,
Line 66, "(10×) pH7" should read --(10X) pH7--.

Column 15,
Line 1, "CaCl$_2$ 5 µLLM" should read --CaCl$_2$ 5 µM--.
Line 2, "micronutriments (10000×)" should read --micronutriments (10000X)--.
Line 4, "FeCl$_3$(100×)" should read --FeCl$_3$(100X)--.

Column 17,
Line 35, "(10×) pH7" should read --(10X) pH7--.
Line 38, "micronutriments (10000×)" should read --micronutriments (10000X)--.
Line 40, "FeCl$_3$(100×)" should read --FeCl$_3$(100X)--.
Line 42, "at TO" should read --atT0--.
Line 46, "times: TO" should read --times: T0--.

Signed and Sealed this
Twenty-ninth Day of March, 2016

Michelle K. Lee
*Director of the United States Patent and Trademark Office*

IN THE SPECIFICATION

Column 18,
Line 31, "(10×) pH7" should read --(10X) pH7--.
Line 34, "micronutriments (10000×)" should read --micronutriments (10000X)--.
Line 36, "FeCl$_3$(100×)" should read --FeCl$_3$(100X)--.

IN THE CLAIMS

Column 20,
Line 48, "maltose trehalose" should read --maltose, trehalose--.
Line 49, "rhamno, galactose" should read --rhamnose, galactose--.
Lines 65-66, "Bacterium is" should read --bacterium is--.

Column 21,
Line 12, "Biomass comprises celluloses" should read --biomass comprises cellulose--.